US006830760B2

(12) United States Patent
Cave et al.

(10) Patent No.: US 6,830,760 B2
(45) Date of Patent: Dec. 14, 2004

(54) GLYBURIDE COMPOSITION

(75) Inventors: Gillian Cave, Ellesmere Port (GB); Sarah J. Nicholson, Helsby (GB)

(73) Assignee: Bristol-Myers Squibb Company, Princeton, NJ (US)

( * ) Notice: Subject to any disclaimer, the term of this patent is extended or adjusted under 35 U.S.C. 154(b) by 41 days.

(21) Appl. No.: 10/426,211

(22) Filed: Apr. 30, 2003

(65) Prior Publication Data

US 2003/0185880 A1 Oct. 2, 2003

Related U.S. Application Data

(63) Continuation of application No. 09/735,334, filed on Dec. 12, 2000, now abandoned, which is a continuation-in-part of application No. 09/483,703, filed on Jan. 14, 2000, now abandoned.

(51) Int. Cl.[7] ............................. A61K 9/14; A61K 9/20; A61K 9/48
(52) U.S. Cl. ....................... 424/465; 424/451; 424/452; 424/464; 424/489
(58) Field of Search .............................. 424/451, 452, 424/464, 465, 489

(56) References Cited

U.S. PATENT DOCUMENTS

| | | | | |
|---|---|---|---|---|
| 3,174,901 | A | * 3/1965 | Sterne ........................ | 514/635 |
| 3,979,520 | A | 9/1976 | Rothe et al. ................ | 424/321 |
| 4,060,634 | A | * 11/1977 | Rothe et al. ................ | 514/593 |
| 4,916,163 | A | 4/1990 | Ni .............................. | 514/593 |
| 5,631,224 | A | 5/1997 | Efendic et al. .............. | 514/12 |
| 5,663,198 | A | 9/1997 | Reul et al. .................. | 514/471 |
| 5,922,769 | A | * 7/1999 | Barelli et al. ............... | 514/616 |
| 5,932,245 | A | 8/1999 | Wunderlich et al. ........ | 424/451 |
| 5,965,584 | A | 10/1999 | Ikeda et al. ................. | 514/342 |
| 6,153,632 | A | 11/2000 | Rieveley ..................... | 514/369 |
| 6,318,650 | B1 | * 11/2001 | Breitenbach et al. ........ | 241/23 |
| 2003/0077297 | A1 | * 4/2003 | Chen et al. ................. | 424/400 |

FOREIGN PATENT DOCUMENTS

| | | |
|---|---|---|
| AU | A-42302/89 | 9/1989 |
| EP | 0362704 B2 | 8/1996 |
| GB | 1358727 | 9/1971 |
| RU | 2026670 C1 | 1/1995 |
| RU | 2000109583 A | 1/2002 |
| WO | WO97/17975 | 5/1997 |
| WO | WO98/57634 | 12/1998 |
| WO | WO99/03476 | 1/1999 |

OTHER PUBLICATIONS

Reaven et al., "Combined Metformin–Sulfonylurea Treatment of Patients with Noninsulin–Dependent Diabetes in Fair to Poor Glycenmic Control", Journal of Clinical Endocrinology and Metabolism, vol. 74, No. 5, pp 1020–1026, 1992.*
Package insert "Bi–Euglucon M".*
Package insert "Suguan M".*
Vigneri et al, "Treatment of NIDDM Patients with Secondary Failure to Glyburide: Comparison of the Addition of Either Metformin or Bed–Time NPH Insulin to Glyburide", Diabete & Metabolisme, 1991, 17, 232–234.
Higginbotham et al, "Double–Blind Trial of Metformin in the Therapy of Non–Ketotic Diabetes", The Med. Journal of Australia, Aug. 11, 1979, 154–156.
Edwards et al, Combination Glipizide/Metformin Treatment Reduces Low Density Lipoprotein Binding to Arterial Proteglycane in NIDDM, Diabetes, (46, Suppl. 1, 45A, 1997).
Cefalu et al, "Combination of glipizide/Metformin Normalizes Glucose and Improves Insulin Sensitivity in Hyperinsulinemia Moderately Well Controlled", Diabetes (45, Suppl. 2, 201A, 1996).
Crouse et al, "Effects of Combination of Glipizide/Metformin Treatment on Oxidizability of LDL in NIDDM", Circulation (94, No. 8, Suppl., I508, 1996).
Cefalu et al, "Insulin Sensitivity is Improved After Glipizide Monotherapy and Combination with Metformin", Diabetologia (39, Suppl. 1, A231, 1996).
Reaven et al, "Combined Metformin–Sulfonylurea Treatment of Patients with Noninsulin–Deendent Diabetes in Fair to Poor Glycemic Control", J. Clin. Endocrinol. Metab. (74, No. 5, 1020–26, 1992).
Hollenbeck et al, "Combination Glipizide/Metformin Treatment in Non–Insulin Dependent Diabetes (NIDDM)", Diabetes (39, Suppl. 1, 108A, 1990).
Press Release Sep. 30, 1999: Bristol–Myers Squibb Files New Drug Application for Novel Oral Antidiabetic Drug.
GLUCOMIDE—Italian Package Insert, Repertorio Farmaceutico Italiano, 1999—with English translation.
GLIBOMET—Italian Package Insert, Repertorio Farmaceutico Italiano, 1999—with English translation.
Suguan M—Italian Package Insert, Repertorio Farmaceutico Italiano, 1999—with English translation.
Bi–Euglucon M—Italian Package Insert, Repertorio Farmaceutico Italiano, 1999—with English translation.
Haupt et al, "Oral Antidiabetic Combination Therapy with Sulfonyl Ureas and Metformin", Med. Welt. (40, No. 5, 118–23, 1989).
Parodi et al, "Results with a Combination of Glipizide and Dimethylbiguanide in 40 Cases of Diabetes", Gass. Med. Ital., 132/5 (226–235) 1973.

(List continued on next page.)

Primary Examiner—Thurman K. Page
Assistant Examiner—S. Tran
(74) Attorney, Agent, or Firm—Burton Rodney

(57) ABSTRACT

The present invention relates to a physical form of the known drug substance glyburide, also known as glibenclamide, and chemically defined as 5-chloro-N-[2-[4-[[[(cyclohexylamino)-carbonyl]amino]sulfonyl]phenyl]ethyl]-2-methoxybenzamide (Merck Index, Tenth Edition, p. 642), as well as to dosage forms, e.g., tablets and capsules, incorporating said physical form of glyburide.

11 Claims, No Drawings

OTHER PUBLICATIONS

Borchert et al, "Zur biologischen Verfugbarkelt von Glibenclamid in Abhangigkeit von der TeilchengroBe" Pharmazie, vol. 31, No. 5, May 1976 (2976–05) p. 307–309.

Arnqvist et al, "Pharmacokinetics and Effects of Glibenclamide in Two Formulations, HB 419 and HB 420, in Type 2 Diabetes", Annals of Clinical Research, vol. 15, Suppl. 37, 1983, p. 21–25, XP002165768.

Erle, G. et al, "A comparison of preconstituted, fixed combinations of low–dose glyburide plus metformin versus high–dose glyburide alone in the treatment of type 2 diabetic patients", Acta Diabetol, 36:61–65, 1999.

Hermann, L.S., "Therapeutic Comparison of Metformin and Sulfonylurea, Alone and in Various Combinations", Diabetes Care, vol. 17, No. 10, Oct. 1994.

* cited by examiner

GLYBURIDE COMPOSITION

This application is a continuation of application Ser. No. 09/735,334, filed Dec. 12, 2000, now abandoned, which is a continuation-in-part of U.S. application Ser. No. 09/483,703 filed Jan. 14, 2000 now abandoned.

The present invention relates to a physical form of the known drug substance glyburide, also known as glibenclamide, and chemically defined as 5-chloro-N-[2-[4-[[[(cyclohexylamino)-carbonyl]amino]sulfonyl]phenyl]ethyl]-2-methoxybenzamide (Merck Index, Tenth Edition, p. 642), as well as to dosage forms, e.g., tablets and capsules, incorporating said physical form of glyburide.

Specifically, the physical form of glyburide which is the subject matter of this invention is glyburide having a defined particle size distribution. This particle size distribution provides an enhanced rate of dissolution of the glyburide compared to bulk glyburide, and it provides reproducible bioavailability in vivo. The glyburide of the invention can also be incorporated into a tablet or capsule matrix to enhance the physicochemical (e.g., rate of drug dissolution and absorption) properties desired. The preferred rates of dissolution and absorption herein provide for early onset of glyburide absorption, yet avoid the very high and rapidly achieved plasma drug concentrations ("spike") that would be achieved with prior art formulations when attempting to provide for early onset of absorption. A very high and rapidly achieved concentration can lead to undesirable hypoglycemia. The glyburide of the physical form described in this invention achieves this early rate of absorption, yet also maintains exposure of the patient to drug (as measured by the area under the plasma drug concentration against time curve), and therefore maintains the efficacy of the formulation.

The glyburide of the subject invention, and formulations based on this material, have properties that are particularly suitable for use as oral preprandial secretagogues.

Glyburide of the physical form described in this invention can also be used in formulations combining it with other drugs used in the treatment of type II diabetes. Examples include, but would not be limited to, acarbose or other glycosidase inhibitors, rosiglitazone, pioglitazone or other thiazolidonediones, biguanides such as metformin fumarate, repaglinide and other "aglinides". Glyburide with the particle size distribution as given in the current invention may be particularly useful in cases where co-formulation with drugs of high dose and high solubility are required. An example of such a drug used for the treatment of type II diabetes is the biguanide known as metformin (including its fumarate and hydrochloride salts).

Glyburide is a commercially available product indicated for the treatment of type II diabetes. Its mode of action is that of an insulin secretagogue, i.e., that of an agent which stimulates the secretion of insulin from patient's beta cells. (See U.S. Pat. Nos. 3,426,067; 3,454,635; 3,507,961 and 3,507,954.) Subsequent to the discovery of glyburide itself, glyburide compositions with enhanced bioavailability to that of the originally developed and marketed formulation became available, for example as described in U.S. Pat. No. 3,979,520 and 4,060,634. These patents describe the use of micronized or high surface area (e.g., 3 to 10 $m^2/g$) glyburide in combination with various pharmaceutically acceptable excipients to obtain enhanced bioavailability. Another composition in the prior art relates to the use of a spray dried lactose formulation of micronized glyburide having a narrow distribution of particle sizes. The spray dried lactose in said composition is the preponderant excipient (not less than 70% of the final composition.)

U.S. Pat. No. 5,258,185 describes rapidly absorbable formulations of glyburide prepared by dissolving the drug in liquid polyethylene glycol and/or an alcohol (e.g., ethanol) with a sugar alcohol (e.g., sorbitol) solution and optionally an alkalizing agent (e.g., ammonia). This solution is blended with suitable powdered pharmaceutically acceptable excipients to provide a dry granulation material suitable for compression into tablets. Similarly, Ganley (J. Pharm. Pharmac., 36:734–739, 1984) describes an improved formulation of glyburide by including solid polyethylene glycol in a capsule formulation, and Shaheen (Int. J. Pharm., 38:123–131, 1987) uses polyethylene glycol and an alkalizing agent, tromethamine, to provide for rapid glyburide release from a tablet formulation.

Because of the poor water solubility of glyburide, the rate of dissolution of the drug from a dosage form is a controlling factor in determining the rate and extent of drug absorption. The rate of dissolution depends on particle size (or particle surface area, which can be related to particle size). Borchert (Pharmazie, 31:307–309,1976) demonstrated the importance of this in vivo where studies in rats and dogs showed more extensive absorption of glyburide when a fine particle size material was evaluated against a coarser material, the drug being administered as a suspension. Arnqvist et al (Ann. Clin. Res., 15: 21–25, 1983) showed it was possible to micronize glyburide to such an extent that the reduced particle size of glyburide provided, relative to the reference formulation, higher maximum serum concentrations and greater area under the serum concentration time curve after dosing a tablet containing a reduced amount of drug.

None of these studies however show how to define properly the limits of particle size properties required in order to provide for appropriate bioavailability from a solid dosage form containing glyburide. It has been found that the appropriate bioavailability for glyburide is obtained when the particle size reduction of the glyburide is controlled so as not to provide what is classically accepted as "micronized" material, yet is fine enough to provide for the desired rate of dissolution. Also helpful for obtaining the appropriate bioavailability is the choice of excipients used in the formulation. The preferred excipients, known in the art, would be those that allow drug release to occur without substantially influencing the rate of drug dissolution and hence absorption. Such excipients would be highly soluble in water, and hence dissolve rapidly when the dosage form is immersed in an aqueous environment. In this way, the poorly soluble glyburide is liberated as a finely divided suspension. Dissolution of glyburide from this suspension, the rate of which is controlled by the particle size distribution of the suspension, is a prerequisite for absorption. Hence, the absorption characteristics are defined by the particle size distribution of the glyburide. In this way, as modeled by in vitro testing, the preferred dosage form is rapidly converted to a suspension of glyburide particles when the dosage form is ingested. Poorly soluble excipients may result in a dosage form that erodes too slowly. For example, dosage forms prepared with the insoluble excipient dicalcium phospate show slow erosion and consequently slow liberation of glyburide. Some currently marketed glyburide formulations, for example Micronase™, employ such excipients, and as a result can exhibit relatively slow liberation of glyburide into solution. Tablets and capsules prepared according to the current invention using soluble excipients released 80% of their contained glyburide within 20 minutes in a medium of pH 6.4 phosphate buffer with 1% w/w sodium dodecyl sulphate medium and agitation conditions of paddles at 50 rpm.

The appropriate bioavailability of glyburide avoids rapidly achieving a very high maximum ("spiked") drug concentration in blood plasma. A very high concentration can predispose the patient to undesirable hypoglycemia. Additionally, the appropriate bioavailability of glyburide provides for the adequate extent of drug absorption such that an area under the plasma drug concentration against time curve maintains efficacy. While not being bound by any theory, it appears that it is this combination, i.e., the early onset of glyburide absorption, without producing excessively high maximum plasma drug concentrations, yet also maintaining exposure of the patient to the drug, that permits the glyburide of this invention to be employed as an oral preprandial secretagogue.

Other drug substances may be co-formulated with glyburide as well and still allow for appropriate glyburide bioavailability. In particular, combination tablets or capsules for multiple drug therapy of diabetes is contemplated.

Data from studies with metformin hydrochloride/glyburide tablets formulated with glyburide of different particle size characteristics allowed for the development of a correlation between glyburide particle size and the in vivo performance. The properties of the lots of glyburide used in the series of combination tablets employed are shown in the table below. The desired particle size distribution may be obtained by sieving or, preferably, air jet milling, and was measured by a laser light scattering method.

| | Glyburide particle size (microns) | | |
|---|---|---|---|
| Tablet batch | 25% undersize | 50% undersize | 75% undersize |
| Combo 1 | 15 | 33 | 62 |
| Combo 2 | 28 | 58 | 88 |
| Combo 3 | 10 | 25 | 52 |
| Combo 4 | 6 | 11 | 19 |

When four compositionally-identical individual batches of tablets of metformin hydrochloride-glyburide 500/2.5 mg were prepared using each of these lots of glyburide and dosed to humans, the following pharmacokinetic parameters were found on analysis of the glyburide plasma concentration-time curves:

| | Pharmacokinetic parameters, glyburide | | | |
|---|---|---|---|---|
| Tablet batch | Cmax (ng/ml, geo.mean) | AUC (ng/ml/hr, geo.mean) | Cmax (ng/ml, arith.mean) | AUC (ng/ml/hr, arith.mean) |
| Combo 1 | 71 | 478 | 76 | 493 |
| Combo 2 | 52 | 345 | 54 | 339 |
| Combo 3 | 64 | 513 | 67 | 531 |
| Combo 4 | 88 | 642 | 93 | 716 |

A reasonable correlation can be obtained between the particle size and the maximum attained geometric mean glyburide plasma concentration, Cmax, and also the geometric mean area under the glyburide plasma concentration-time curve, AUC.

From these correlations, projected limits on particle size for glyburide that would give predicted Cmax and AUC values ±25% of a mean value for batches of the reference glyburide formulation, Micronase™, utilized in the in vivo studies were calculated.

Accommodating both Cmax and AUC requirements, the projected particle size limits then become:

| 25% undersize limits | 50% undersize limits | 75% undersize limits |
|---|---|---|
| 3–11 microns | 6–23 microns | 15–46 microns |

The particle size measurement method of laser light scattering uses drug substance dispersed in liquid paraffin for introduction into the measurement cell. The apparatus produces a volume based, cumulative size distribution. Based on the above data and this methodology, it was found that the preferred particle sizes for glyburide to assure reproducibility of dissolution and bioavailability are:
  25% undersize value between 4 and 7 microns,
  50% undersize value between 7 and 13 microns, and
  75% undersize value between 17 and 23 microns.
Particularly preferred particle sizes for glyburide are:
  25% undersize value not more than 6 microns,
  50% undersize value not more than 7 to 10 microns, and
  75% undersize value not more than 21 microns.

These limits can thus be placed on the glyburide to assure reproducibility and appropriate bioavailability each time the drug substance is prepared and used in tablet or capsule formulation.

Glyburide having these particle size characteristics have powder surface area values in the range of about 1.7 to 2.2 $m^2g^{-1}$ as determined by nitrogen adsorption. This is yet another difference between the glyburide of the invention and that of the prior art. The glyburide of the prior art generally required its powder surface area to be in excess of 3 $m^2g^{-1}$ (preferably 5 to 10 $m^2g^{-1}$) to yield appropriate glyburide bioavailability. The glyburide of particle size properties detailed herein produces appropriate glyburide bioavailability in humans.

When formulating the glyburide into a tablet or capsule, it is preferable to include in the formulation a suitable level of highly water-soluble excipients. Such excipients are generally soluble in water from 50 mg/ml to in excess of 300 mg/ml. They can be used singly or in combination and may comprise 45 to 90% by weight of the total formulation. Such a material used in a tablet or capsule formulation will completely dissolve within 5 to 30 minutes when subjected to an in vitro drug release test procedure, liberating the suspension of glyburide particles. The formulation may also include a binder such as povidone or low viscosity hydroxypropyl methylcellulose and a lubricant, such as magnesium stearate or sodium stearyl fumarate. The inclusion of a disintegrant has been found to be highly desirable to assure the rapid break up of the dosage form when immersed in an aqueous environment. Suitable disintegrants include croscarmellose sodium or sodium starch glycollate. The formulation may optionally include other excipients such as glidants, anti-adherents, colors, flavors, film coating components (including polymers such as hydroxypropyl methylcellulose, wetting agents such as polysorbate 20, plasticizers such as polyethylene glycol 200), and other materials commonly used in the formulation of tablets and capsules and as would be familiar to those skilled in the art.

Suitable highly water soluble excipients would also include, but not be limited to, sugar alcohols such as mannitol, sorbitol and xylitol; sugars such as sucrose, lactose, maltose and glucose; oligosaccharides such as maltodextrins.

EXAMPLE 1

Glyburide

Bulk glyburide was introduced into an air jet mill (Esco Strahlmuehle) via a hopper equipped with a screw feed, and the speed of charge was set at 20 to 30 kg/hour. The mill was operated with a Venturi nitrogen pressure of approximately 1.5 atmospheres and a micronization chamber pressure of 4 atmospheres. Size reduction was not allowed to proceed to the extent normally employed to make glyburide that would be described as micronized. The mill was turned off and the drug substance was discharged from it. A sample of the size-reduced glyburide was evaluated by a laser diffraction particle size analysis method. The following results were obtained:

D25% 5 microns, D50% 9 microns, D75% 21 microns (Note: Such a size reduction process in the mill normally would be allowed to proceed to produce typical micronized material of commerce. A commercially available micronized sample was tested by the particle size analysis method and the following results obtained:

D25% 2.8 microns, D50% 4.5 microns, D75% 7.3 microns.

Hence the material of this Example is different from the commercially available micronized glyburide sample tested.)

EXAMPLE 2

The following single entity glyburide formulation was prepared.

| Ingredient | mg per Tablet |
| --- | --- |
| Mannitol | 150.0 |
| Glyburide of Example 1 | 5.0 |
| Croscarmellose sodium | 6.25 |
| Microcrystalline cellulose | 75.0 |
| Povidone | 12.5 |
| Magnesium stearate | 0.2–2.5 |

The glyburide was blended with the croscarmellose sodium and that mixture was blended with the mannitol. The resulting blend was wet granulated using the povidone dissolved in an appropriate amount of purified water. The granules obtained were dried to an appropriate residual moisture content, mixed with the microcrystalline cellulose, lubricated by mixing with the magnesium stearate and compressed into tablets each containing 5 mg of glyburide.

The tablets were subjected to an in vitro dissolution method to determine the rate at which the glyburide was released from the tablets. The tablets were placed into a dissolution medium of pH 6.4 phosphate buffer with 1% w/w sodium dodecyl sulphate, and stirred with paddles at 50 rpm. It was found that 80% of the drug in the tablet was dissolved within 20 minutes.

EXAMPLE 3

| Ingredient | mg. per Tablet |
| --- | --- |
| Mannitol | 250.0 |
| Glyburide of Example 1 | 1.25 |
| Croscarmellose sodium | 7.0 |
| Microcrystalline cellulose | 28.25 |
| Povidone | 10.0 |
| Magnesium stearate | 0.6–6.0 |
| Film coat (optional) | 4.5–12.0 |

A process similar to the process described in Example 2 would yield tablets containing 1.25 mg of glyburide. The tablets are optionally film coated with a proprietary film coat composition such as OPADRY, employing a side vented coating pan.

EXAMPLE 4

| Ingredient | mg per tablet |
| --- | --- |
| Lactose monohydrate | 250.0 |
| Glyburide of example 1 | 5.0 |
| Croscarmellose sodium | 7.0 |
| Microcrystalline cellulose | 28.25 |
| Povidone | 10.0 |
| Magnesium stearate | 0.6–6.0 |

A process similar to the process described in Example 2 yielded tablets containing 5.0 mg of glyburide.

EXAMPLE 5

The glyburide of the invention can be co-formulated with other drugs for the treatment of type II diabetes. This would facilitate treatment for patients having to take multiple medications when single drug therapy is inadequate to control their disease. Such agents might include, but would not be limited to, acarbose or other glycosidase inhibitors, rosiglitazone, pioglitazone or other thiazolidonediones, biguanides such as metformin fumarate, repaglinide and other "aglinides".

Example with Rosiglitazone Maleate

| Ingredient | mg. per Tablet |
| --- | --- |
| Mannitol | 250.0 |
| Rosiglitazone maleate | 2.65 |
| Glyburide of Example 1 | 1.25 |
| Croscarmellose sodium | 7.0 |
| Microcrystalline cellulose | 28.25 |
| Povidone | 10.0 |
| Magnesium stearate | 0.6–6.0 |

*equivalent to 2 mg of rosiglitazone

By a process similar to the process described in Example 2, the two drug substances are first blended with the croscarmellose sodium and the remaining ingredients are then added to provide tablets, each containing 1.25 mg of glyburide and 2 mg of rosiglitazone (as the maleate salt).

Those of ordinary skill in the art will appreciate that the embodiments shown can be modified without departing from the spirit and scope of the invention.

What is claimed is:

1. A table or capsule comprising a substance 5-chloro-N-[2-[4-[[[(cyclohexylamino)-carbonyl]amino]sulfonyl]phenyl]ethyl]-2-methoxybenzamide having the following particle size distribution characteristics:

25% undersize value between 3 and 11 µm,

50% undersize value between 6 and 23 µm, and

75% undersize value between 15 and 46 µm and a second drug, wherein the second drug being a drug that is useful for the treatment of type II diabetes.

2. The table or capsule of claim 1 wherein the particle size distribution of the substance is 25% undersize value between 4 and 7 μm,
50% undersize value between 7 and 13 μm, and
75% undersize value between 17 and 23 μm.

3. The tablet or capsule of claim 1 wherein the second drug is selected from the group consisting of glycosidase inhibitors, thiazolidonediones, biguanides and aglinides.

4. The tablet or capsule of claim 3 wherein the second drug is selected from the group consisting of acarbose, rosiglitazone, pioglitazone, metformin fumarate and repaglinide.

5. The tablet or capsule further comprising and at least one highly water soluble excipient.

6. The tablet or capsule of claim 5 wherein the at least one highly water soluble excipient comprises 45 to 90% by weight of the total formulation.

7. A method of treating type II diabetes which comprises administering to a patient in need of such treatment a therapeutically effective amount of the substance of claim 1.

8. The substance 5-chloro-N-[2-[4-[[[(cyclohexylamino)-carbonyl]amino]sulfonyl]phenyl]ethyl]-2-methoxybenzamide having the following particle size distribution characteristics:
25% undersize value not more than 6 microns,
50% undersize value not more than 7 to 10 microns, and
75% undersize value not more than 21 microns and a second drug, wherein the second drug being a drug that is useful for the treatment of type II diabetes.

9. A tablet or capsule comprising a combination of metformin and glyburide having the following particle size distribution characteristics:
25% undersize value between 3 and 11 μm,
50% undersize value between 6 and 23 μm, and
75% undersize value between 15 and 46 μm.

10. The tablet or capsule as defined in claim 9 wherein the glyburide has a particle size distribution, which is
25% undersize value between 4 and 7 μm,
50% undersize value between 7 and 13 μm, and
75% undersize value between 17 and 23 μm.

11. The tablet or capsule as defined in claim 9 wherein the glyburide has the following particle size distribution characteristics:
25% undersize value not more than 6 microns,
50% undersize value not more than 7 to 10 microns, and
75% undersize value not more than 21 microns.

* * * * *

UNITED STATES PATENT AND TRADEMARK OFFICE
CERTIFICATE OF CORRECTION

PATENT NO. : 6,830,760 B2  
DATED : December 14, 2004  
INVENTOR(S) : Gillian Cave et al.

Page 1 of 1

It is certified that error appears in the above-identified patent and that said Letters Patent is hereby corrected as shown below:

Column 6,
Line 63, after "46$\mu$m" and before "and", insert -- ; --.

Column 8,
Line 1, after "microns" and before "and", insert -- ; --.

Signed and Sealed this

Fifteenth Day of November, 2005

JON W. DUDAS  
*Director of the United States Patent and Trademark Office*